United States Patent
Dörr et al.

[11] Patent Number: 5,100,530
[45] Date of Patent: Mar. 31, 1992

[54] ELECTROCHEMICAL DETECTOR

[75] Inventors: Thomas Dörr; Clemens Linowski, both of Walbronn, Fed. Rep. of Germany

[73] Assignee: Hewlett-Packard Company, Palo Alto, Calif.

[21] Appl. No.: 568,099

[22] Filed: Aug. 16, 1990

[30] Foreign Application Priority Data

Sep. 15, 1989 [EP] European Pat. Off. ...... 89-117-114.2

[51] Int. Cl.$^5$ .......................................... G01N 27/26
[52] U.S. Cl. .................... 204/406; 204/412; 422/70
[58] Field of Search ............ 204/406, 412; 422/70

[56] References Cited

U.S. PATENT DOCUMENTS

| | | | |
|---|---|---|---|
| 4,227,988 | 10/1980 | Galwey et al. | 204/406 X |
| 4,366,033 | 12/1982 | Richter et al. | 204/406 X |
| 4,498,039 | 2/1985 | Galwey et al. | 204/406 X |
| 4,499,423 | 2/1985 | Matthiessen | 204/406 X |
| 4,506,226 | 3/1985 | Luce et al. | 204/406 X |
| 4,642,172 | 2/1987 | Fruhwald | 204/406 X |
| 4,664,886 | 5/1987 | Novack et al. | 204/406 X |

Primary Examiner—Nam X. Nguyen
Attorney, Agent, or Firm—Woodcock, Washburn, Kurtz, Mackiewicz & Norris

[57] ABSTRACT

An electrochemical detector comprising an electrochemical cell (11), a working electrode (1), an auxiliary electrode (2), a reference electrode (3), a potentiostat (4), and a circuit (7,8) for deriving a signal indicative of the current developed at the working electrode additionally comprises means for monitoring and determining the potential of the reference electrode (3). These means comprise an electrometer circuit (9) which can be connected via a switch (S2) to the auxiliary electrode (2) to measure the potential of the reference electrode. During the measurement, the working electrode (1) is disconnected from the circuit (7,8) which is at the same time connected to the electrometer circuit (9) via switch (S1). The invention permits to recognize measuring errors associated with instabilities in the reference electrode potential (FIG. 1).

9 Claims, 1 Drawing Sheet

ELECTROCHEMICAL DETECTOR

BACKGROUND OF THE INVENTION

The invention relates to an electrochemical detector for detecting electroactive substances, i.e., substances which are either oxidizable or reducible. Such detectors belong to the most sensitive and most specific detectors presently available and are of particular advantage in liquid chromatography where they are used to detect the liquid eluting from the separation column.

An electrochemical detector for detecting electroactive substances is known, for example, from EP-A-140286. This known electrochemical detector comprises an electrochemical cell into which the liquid to be analyzed is introduced and in which three electrodes are arranged: a working electrode, a counter electrode (also denoted as auxiliary electrode), and a reference electrode. The electrochemical process is made to occur at the working electrode and the reference electrode compensates for any change in the conductivity of the mobile phase transporting the substances to be analyzed. The potential near the counter electrode is held at a fixed value by a control circuit commonly denoted as "potentiostat". The potential near the counterelectrode is sensed by the reference electrode which is connected to the potentiostat. When a substance to be analyzed arrives at the surface of the working electrode, a current is developed which is converted by an electrometer to a voltage output which can then be processed by further circuitry.

In the prior art according to EP-A- 140286, the liquid to be analyzed impinges perpendicularly onto the working electrode in the form of a liquid jet; this type of detector design is called "wall jet design". Other detector designs employing a three-electrode configuration are also possible, for example the "thin-layer design" wherein the liquid flows past the working electrode. In both designs, reference electrodes are used which comprise a redox couple, such as the commonly used Ag-/Ag+Cl- redox couple.

There are several potential sources of error in an electrochemical detector which may lead to inaccurate measuring results. Such errors typically lead to a shift of the so-called "half wave potential". The term "half wave potential" will be shortly explained: When the potential of the working electrode versus the reference electrode (where both of them are referred to ground) is increased and the current measured at the working electrode is plotted as a function of the potential, a characteristic curve results which has a flat portion at low potentials, then a portion where the current increases steeply and then again a substantially flat plateau. The point on this curve where the current value is half of the value of that of the plateau corresponds to a certain potential which is called the half wave potential. In order to have reproducible detection conditions, it is desirable that the half wave potential for a specific substance to be detected remains constant.

It may occur, however, that the half wave potential for a specific substance changes. For example, it is frequently the case that the working electrode is passivated in the course of the electrochemical detection process due to contamination. As a result of this, the curve of current versus potential becomes flattened and the corresponding half wave potential moves to a higher value, thus impairing the reproducibility of the measurement. One way to overcome the problems with passivation of the working electrode is to operate the detector in a pulse mode as described in the above-mentioned prior art, whereby one portion of the pulse cycle serves to clean the working electrode.

Other error sources in an electrochemical detector, particularly when used in connection with a liquid chromatograph, may be due to problems in the liquid delivery like flow ripple or bad degassing or gas bubbles in the electrochemical cell itself. The mentioned error sources may all contribute to an overall error in the detector; the prior art approach to cope with such errors is to eliminate the individual sources of error, for example to provide means for cleaning the working electrode (e.g., by using pulse mode), or to ensure that the flow conditions are as uniform as possible. The potential of the reference electrode may change due to contamination of the electrode or by changes in the ion concentration in the environment of the electrode, and thus also be a source of error. Apparently, however, the reference electrode has not been much considered in the prior art as an error source.

SUMMARY OF THE INVENTION

Relative to the prior art, it is an object of the invention to provide an electrochemical detector which permits one to avoid measuring errors caused by the reference electrode. This object is solved by the features of this invention as claimed herein.

In accordance with the invention, it has been realized that drift in the reference electrode potential or faulty absolute values of this potential may be a source of measuring errors in electrochemical detectors which was previously not taken into account adequately. The invention provides means which permit a user to measure the reference potential in an uncomplicated way with a minimum of additional hardware. The invention provides the possibility to determine the actual reference potential independently of other sources of drift or errors of the potential in the electrochemical detector, such as drift caused by passivation of the working electrode.

It is a basic idea of the invention that the measurement of the reference potential can be performed in a simple way by re-defining the conventional functions of the electrodes in the electrochemical detector: The electrode which functions in the usual electrochemical detection process as the auxiliary electrode performs the function of a working electrode to measure the potential of the reference electrode, whereas the working electrode is switched off so that it cannot interfere with the potential measurement. It is important that the measurement of the potential is currentless because any current flow would disturb the redox reaction at the reference electrode.

The invention ensures a quick and unproblematic switching-over between normal electrochemical detection (amperometry, coulometry) and reference electrode diagnosis. The measured reference potential is displayed to inform the user of any problems with the reference electrode; additionally, circuitry can be provided to enable electrochemical detection only in case that the reference potential is free of drift and has the required absolute value.

Advantageous embodiments of the invention are described hereinafter. For example, it is preferred that the signal processing circuitry which is used in the normal electrochemical detection mode for deriving a signal indicative of the working electrode current is used in the reference electrode diagnosis for signal amplification. Furthermore, the switches for switching over between electrochemical detection mode and reference electrode diagnosis may comprise reed relays which have the advantage of low leakage currents. The invention can be used, for example, in connection with a liquid chromatograph wherein the ions required for the redox couple of the reference electrode are provided by the mobile phase pumped through the separation column. It is understood that the invention can be used for any type of reference electrodes, for example also for reference electrodes of the type known from the above mentioned prior art EP-A- 140286, i.e., reference electrodes with internal electrolyte.

BRIEF DESCRIPTION OF THE DRAWINGS

Subsequently, an embodiment of the invention is explained with reference to the drawings.

DETAILED DESCRIPTION OF THE INVENTION

Figure 1:
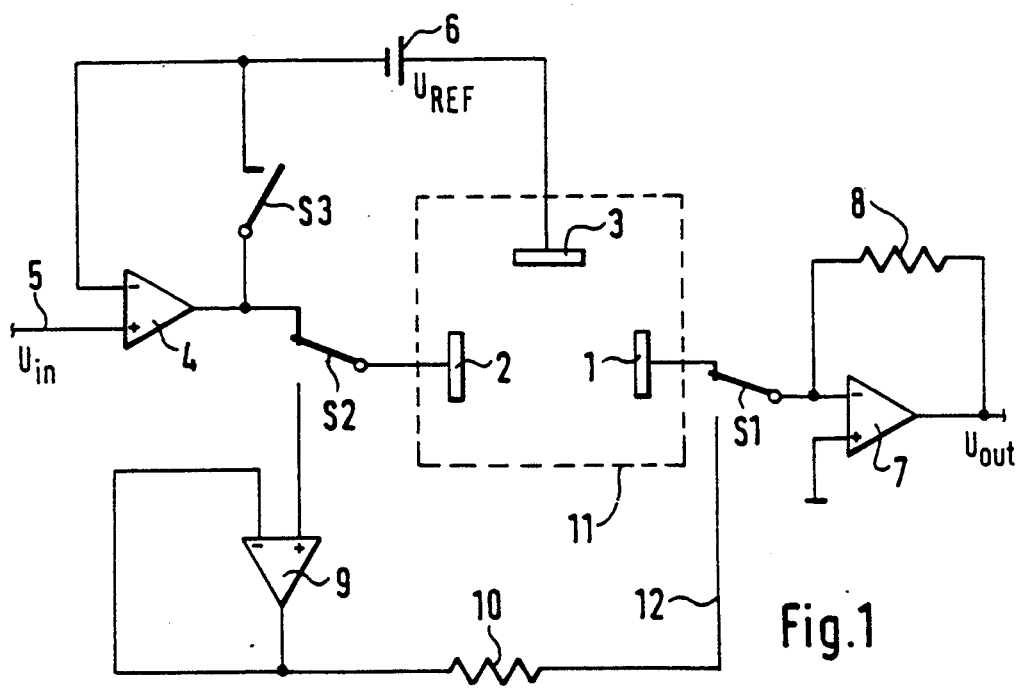
FIG. 1 is a schematic diagram of an electrochemical detector according to the invention illustrating the mode of operation used for electrochemical detection of substances.

FIG. 1 schematically shows basic components of an electrochemical detector of the invention arranged in its normal mode of operation to detect electroactive substances. A working electrode 1, a counter electrode or auxiliary electrode 2, and a reference electrode 3 are arranged in an electrochemical cell into which the liquid to be analyzed is introduced. The cell may be of any type, such as a flow-through cell into which the effluent of a liquid chromatographic separation column is introduced or a cell wherein the liquid to be analyzed is stagnant. Also, the electrochemical cell may be a thin-layer cell or a wall jet cell.

The auxiliary electrode 2 is connected via a switch S2 to the output of an operational amplifier 4. The positive input of operational amplifier 4 is connected to a line 5 on which an input voltage Uin can be applied. The inverting input of operational amplifier 4 is connected to the reference electrode 3. Operational amplifier 4 is operated in a closed loop mode, with the reference electrode serving as a probe to feed back information on the potential of the liquid in the cell for comparison with the applied value Uin. This arrangement of operational amplifier 4 which serves to maintain a constant potential difference between the liquid in the cell and the working electrode is commonly called "potentiostat".

The working electrode 1 is connected via a switch S1 to the inverting input of an operational amplifier 7. The non-inverting input of operational amplifier 7 is connected to ground and a resistor 8 is arranged in the feedback loop of the operational amplifier 7. This circuitry functions as a current-to-voltage converter which provides an output voltage Uout which is proportional to the current received from the working electrode 1 and to the resistance value of resistor 8. The output voltage Uout can either be fed to a suitable recorder or through an additional signal processing circuitry (amplifiers, filters) to a recorder or display means. In a preferred embodiment, the output signal of operational amplifier 7 is fed to an A/D converter wherein it is converted to digital signals which can subsequently be further processed by digital circuitry. With the positions of the switches S1, S2, and S3 being such as shown in FIG. 1, the circuit works as an electrochemical detector for detecting electroactive substances. Due to the shown switch position, the branch of the circuit comprising operational amplifier 9 and resistor 10 are decoupled and do not play a role in the electrochemical detection mode of operation. It is only important to ensure that there does not exist any current leakage path at switch S1.

The reference electrode 3 can be of any known type, for example a metal which is immersed in a solution of its salts, such as a silver wire immersed in a solution of silver chloride (AgCl) as described in the above mentioned prior art EP-A- 140286, having a well-defined concentration of chlorine ions. In FIG. 1, the redox couple constituting the reference electrode is indicated at reference numeral 6. The reference electrode may have an internal electrolyte coupled to the eluent in the electrochemical cell via an "ion bridge" such as a membrane or porous material. According to Nernst's law, the potential of the used redox pair is defined by the anion concentration. Consequently, due to diffusion processes out of the reference electrode through the "ion bridge" the reference potential may change.

In another embodiment of the invention, the reference electrode may have a direct liquid connection to the electrochemical cell, that means with no membrane or other "ion bridge" in between. In this case, the ions required for the reference electrode are provided by the liquid in the electrochemical cell, for example in liquid chromatographic applications the eluent flowing through the electrochemical detector. As a practical example, the reference electrode may comprise a silver wire coated with silver chloride and the required chlorine ions are provided in a predetermined concentration by the eluent. With this embodiment of a reference electrode, it may come to reference potential drift, for example if the chlorine concentration in the eluent changes or any other effects influencing the reference potential.

Figure 2:
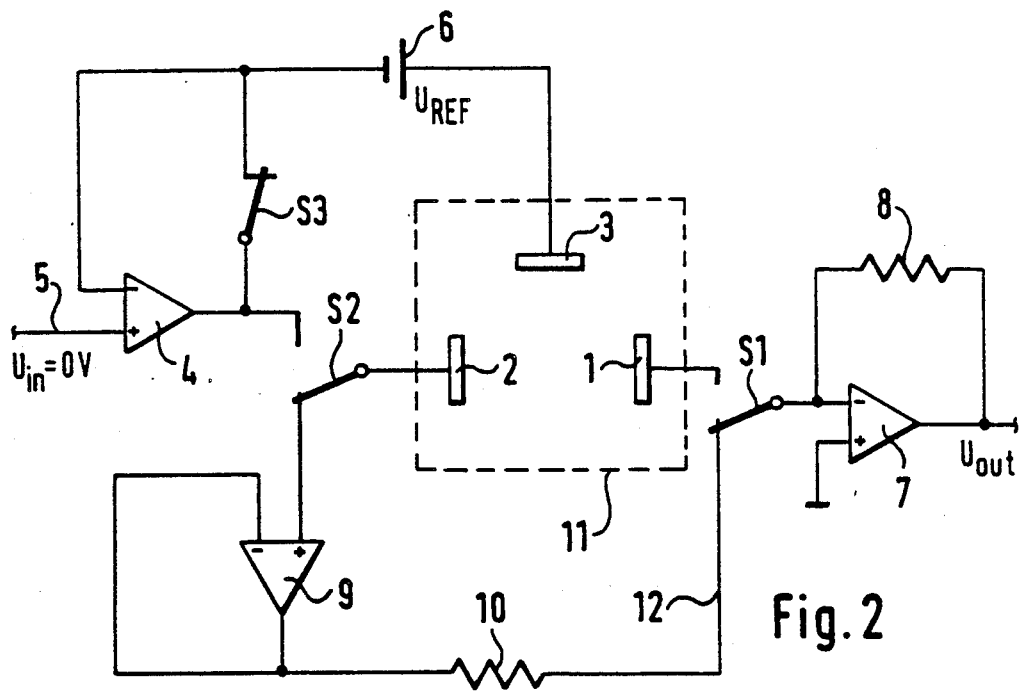
FIG. 2 illustrates the mode of operation of the electrochemical detector of FIG. 1 wherein the reference electrode is tested.

FIG. 2 illustrates the mode of operation wherein the potential of the reference electrode is derived. The circuit components are the same as in FIG. 1, but the positions of the switches are different. Switch S3 is now closed such that the output of operational amplifier 4 is connected to the reference electrode 3. Switch S2 which is a change-over switch is now connected to the non-inverting input of the operational amplifier 9, and the change-over switch S1 is now connected to a line 12 which is connected via a resistor 10 to the output of the operational amplifier 9. The inverting input of operational amplifier 9 is connected to the output of this amplifier as shown in FIG. 2.

With the switch positions as shown in FIG. 2, the working electrode 1 is switched off so that any interference effects such as leaky current paths during the reference measurement are avoided. The auxiliary electrode 2 is decoupled from the potentiostat 4 and connected to the operational amplifier 9 which functions as an electrometer amplifier and voltage follower. The reference electrode is grounded by setting the potential applied at the non-inverting input of operational amplifier 4 to 0, Volts and by closing switch S3. The electrometer output is fed by a certain resistor to the virtual ground of operational amplifier 7. In an alternative to the circuit of FIG. 2, the grounding of the reference electrode could also be accomplished by directly connecting the reference electrode to ground by providing a controllable ground connection. The advantage of that alternative would be a substantially noiseless reference to ground. The embodiment shown in FIG. 2 has the advantage that any additional current leakage paths are avoided.

In the configuration according to FIG. 2, the output voltage of the amplifier 9 equals the potential of the reference electrode which is to be measured. Operational amplifier 9 is designed as an impedance converter which works with a shunt resistance into the virtual ground of operational amplifier 7. The voltage at the output of operational amplifier 7 thus is proportional to the potential UREF to be measured, whereby the proportionality constant is the quotient of the resistance values of resistor 8 and shunt resistor 10. In an embodiment of the invention, the resistance values of resistors 8 and 10 may be 20 Mega Ohm and 1 Mega Ohm, respectively, resulting in an amplification factor of 20. Instead of a single resistor 8 in the feedback loop of operational amplifier 7, the circuit may be modified such that one of several resistors can be switched into the loop by control of a user in order to allow selection of a desired amplification factor.

With the switch positions as shown in FIG. 2, the auxiliary electrode 2 of the electrochemical detection mode (FIG. 1) performs the function of a working electrode, whereas the actual working electrode 1 is switched off. Furthermore, the components 7,8 which are used in the electrochemical detection mode of operation are used for deriving a voltage signal proportional to the potential of the reference electrode. Thus, according to the invention, these components of an electrochemical detector are used for a novel purpose, namely for determining the potential of the reference electrode. In that way, it is also ensured that the measurement of the reference potential is accomplished with a minimum of additional circuitry. It is important that the measuring of the reference potential is a currentless measurement because otherwise the redox reaction in the reference cell would be disturbed.

As explained above, the output voltage of operational amplifier 9 equals the reference electrode potential UREF to be measured. Thus, in an alternative to the embodiment of FIG. 2, it would be possible to use the output signal of operational amplifier 9 directly for deriving an indication of the value of UREF without routing the signal via resistor 10, switch S1 and circuitry 7,8. The embodiment of FIG. 2, however, has certain advantages over such an approach: First, the output signal of operational amplifier 9 usually will require amplication so that the use of the circuit 10,7,8 saves any additional amplification circuitry and also provides the connection to the A/D converter and the following circuits. Furthermore, since the working electrode 1 would have to be switched off during the measurement of the reference potential to avoid any interferences, the switch S1 according to FIG. 2 can be used for a dual purpose, namely for switching off the working electrode 1 as well as for switching the amplification circuitry 7,8 into reference electrode measurement path 3, 2, S2, 9, 10. In summary, the circuit of FIG. 2 permits to determine the reference electrode potential at a minimum of additional circuitry as compared to the circuitry for the electrochemical detection mode.

In the embodiment of the invention described in connection with FIG. 2, operational amplifiers with optimized current and voltage noise behavior and with very low leakage current are used, such as OPA 111 available from the company Burr-Brown. This amplifier has an advantageous current noise behavior because its noise does not increase at lower frequencies but has a substantially constant noise density, even at frequencies below 0.1 Hz.

The switches S1, S2 and S3 should be selected such that no parasitic current paths occur which might disturb the measurement of the reference potential, whereby switch S1 is of particular importance in this respect. In an embodiment of the invention, the switches are reed relays. According to a practical example, the reed relays have a guaranteed isolation resistance of at least 1012 Ohm at a relative humidity of 90% and 40° C. The input currents of the operational amplifiers are in a practical example below 100 femto Ampere. In order to further reduce any current leakage in the circuit of FIG. 1 and 2, a guard technique can be used when the circuit is implemented on a printed circuit board: The signal carrying conductive paths on the printed circuit board are surrounded on the board by conductive paths which have substantially the same potential such that no current leakage from the signal carrying conductive paths can occur.

When the electrochemical detector according to the invention is used as a liquid chromatography detector to detect the effluent of the chromatographic column, it is preferred that the measurement of the reference potential is performed under the same chromatographic conditions as if an actual chromatographic separation were carried out. That means for example that during the measurement of the reference potential the same eluent as with an actual sample separation flows through the electrochemical detector with the same flow rate.

In an embodiment of the invention, the output signal of circuit 7,8 is digitized by an A/D converter and then further processed to derive the numerical value of the reference voltage. This value is displayed by an appropriate display means and thus gives the user an indication if the reference electrode is working properly. For example, when the reference electrode with an internal electrolyte is used, the operator could conclude from an unusual value of the reference potential that the chamber for receiving the electrolyte has become dry. Furthermore, changing values of the reference potential indicate that there is drift in the reference potential so that meaningful, reproducible electrochemical measurements are not possible. The measure to take in that case would be to wait a certain time until the reference potential has stabilized or to refill the original ion concentration for stabilizing at the expected reference potential.

According to an embodiment of the invention, a control circuit is provided for enabling electrochemical detection of substances to be analyzed only in case that the reference potential is substantially free of drift. In connection with a liquid chromatograph, for example, such a control circuit would be operative to allow injection of the sample to be analyzed only if the drift of the reference potential is below a selectable value. A preferred measure of the drift is the derivative of the reference potential curve as a function of time. With such a control circuit it is ensured that the detection of the sample always occurs with stable, reproducible conditions.

We claim:

1. An electrochemical detector for detecting electroactive substances, comprising:
   an electrochemical cell for receiving liquid including the substances to be detected,
   a working electrode, an auxiliary electrode, a reference electrode, each of said three electrodes being in conductive connection with the liquid in the electrochemical cell,
   a potentiostat for maintaining during electrochemical detection a constant potential difference between the liquid in the electrochemical cell and the working electrode, with the potentiostat being coupled during electrochemical detection to the reference electrode and to the auxiliary electrode, and
   signal processing circuitry for deriving an electric signal indicative of the current created at the working electrode by electroactive substances,
   in combination with monitoring means for determining and monitoring the potential of the reference electrode, said monitoring means comprising:
      disconnecting means for disconnecting the working electrode from the signal processing circuitry
      grounding means for applying a predetermined potential to the end of the reference electrode opposite to the end in contact with the electrochemical cell,
      an electrometer circuit being operative to perform a substantially currentless measurement of the potential of the reference electrode, and
      switching means for disconnecting the auxiliary electrode from the potentiostat and for connecting the auxiliary electrode to an electrometer circuit.

2. An electrochemical detector as in claim 1, wherein the disconnecting means are also operative to connect the signal processing circuitry to an output of the electrometer circuit when the working electrode is disconnected from the signal processing circuitry.

3. An electrochemical detector as in claim 1, wherein the measured potential of the reference electrode is displayed to a user.

4. An electrochemical detector as in claim 1, wherein the potential of the reference electrode is capable of being measured several times over a period of time such as to detect any drift of this potential, and wherein electrochemical detection is only enabled if the detected drift is below a predetermined value.

5. An electrochemical detector as in claim 1 wherein:
   the potentiostat comprises an operational amplifier having a non-inverting input connected to a source for providing an adjustable input voltage, and an inverting input connected to the reference electrode,
   the grounding means comprise a grounding-means switch arranged between the output of the operational amplifier and the reference electrode,
   said grounding-means switch being opened during electrochemical detection, and
   said grounding-means switch being closed and the input voltage set to 0 volt during measurement of the potential of the reference electrode.

6. An electrochemical detector as in claim 5, wherein the disconnecting means, the switching means and the grounding means switch comprise reed relays.

7. An electrochemical detector as in claim 1, wherein during measurement of the potential of the reference electrode, the reference electrode is disconnected from the potentiostat and directly connected to a fixed potential.

8. The electrochemical detector as in claim 1 adapted to receive said substances to be detected from the effluent of the separation column of a liquid chromatograph.

9. The electrochemical detector as in claim 8, wherein the reference electrode is a redox couple and wherein the anions of the redox couple are provided by the mobile phase of the liquid chromatograph.

* * * * *